(12) United States Patent
Barry et al.

(10) Patent No.: US 6,183,487 B1
(45) Date of Patent: Feb. 6, 2001

(54) ABLATION DEVICE FOR REDUCING DAMAGE TO VESSELS AND/OR IN-VIVO STENTS

(75) Inventors: Robert Lawrence Barry, Kirkland; Matt Hefner, Puyallup; Tom Hiblar, Everett; Joseph Pearce, Seattle; Natalya Peskin, Redmond; Edward Wulfman, Woodinville, all of WA (US)

(73) Assignee: SCIMED Life Systems, Inc., Maple Grove, MN (US)

( * ) Notice: Under 35 U.S.C. 154(b), the term of this patent shall be extended for 0 days.

(21) Appl. No.: 09/178,450

(22) Filed: Oct. 23, 1998

Related U.S. Application Data

(63) Continuation-in-part of application No. 09/035,734, filed on Mar. 5, 1998, now Pat. No. 6,015,420, which is a continuation-in-part of application No. 08/813,827, filed on Mar. 6, 1997, now abandoned, and a continuation-in-part of application No. 08/812,715, filed on Mar. 6, 1997, now abandoned.

(51) Int. Cl.$^7$ .................................................. A61B 17/22
(52) U.S. Cl. ............................................................ 606/159
(58) Field of Search .................................. 606/159, 192; 604/22

(56) References Cited

U.S. PATENT DOCUMENTS

| Re. 33,569 | 4/1991 | Gifford, III et al. . |
| 1,112,982 | 10/1914 | Conine . |

(List continued on next page.)

FOREIGN PATENT DOCUMENTS

| 867 144 | 2/1953 | (DE) . |
| 0 117 519 A1 | 2/1984 | (EP) . |
| 0 268 228 | 5/1988 | (EP) . |
| 0 427 368 A1 | 5/1991 | (EP) . |
| 0 427 368 B1 | 5/1991 | (EP) . |

(List continued on next page.)

OTHER PUBLICATIONS

International Search Report, International Appliation No. PCT/US99/24320, International Filiing Date: Aug. 19, 1999.

Primary Examiner—Michael Buiz
Assistant Examiner—(Jackie) Tan-Uyen T. Ho
(74) Attorney, Agent, or Firm—Christensen O'Connor Johnson Kindness PLLC

(57) ABSTRACT

An ablation burr has a body provided with an inner circumferential rim and an outer circumferential rim that are concentric and spaced longitudinally by a selected distance along the length of the burr. The outer circumferential rim has a generally smooth convex outer surface that reduces damage to a vessel wall or stent. A leading surface of the burr extends between the inner and outer circumferential rims in a substantially uniform, concave manner. An abrasive, for example, diamond grit, is provided on the leading surface. The burr is selectively rotated by a drive shaft, causing the abrasive leading surface of the burr to ablate unwanted deposits. If desired, a wire extends co-axially through the body such that a distal end of the wire extends out of the distal end of the burr. An abrasive tip may be coupled to the distal end of the wire, and is selectively rotated, to ablate unwanted deposits. The burr may be made of a compressible elastomeric material, to facilitate positioning the burr through restrictive openings, such as the coronary ostia. To prevent the burr from becoming welded to a spring tip at the end of the guide wire, a bearing may be provided at a distal region of the guide wire. The bearing has a dynamic member that acts as a bumper and rotates when the ablation device is advanced to the distal region of the guide wire and contacts the dynamic member. In an alternative embodiment of the invention, the leading surface of the burr includes one or more aspiration ports through which debris that is ablated from the occlusion may be removed from a patient's vessel.

3 Claims, 9 Drawing Sheets

FOREIGN PATENT DOCUMENTS

| | | |
|---|---|---|
| 0 086 048 | 8/1993 | (EP) . |
| 2 020 557 | 5/1979 | (GB) . |
| WO 92/03097 | 3/1992 | (WO) . |
| WO 92/03098 | 3/1992 | (WO) . |
| WO 93/01753 | 2/1993 | (WO) . |
| WO 93/01849 | 2/1993 | (WO) . |
| WO 93/19679 | 10/1993 | (WO) . |
| WO 94/10919 | 5/1994 | (WO) . |
| 98 02101 | 1/1998 | (WO) . |
| 98 38928 | 9/1998 | (WO) . |

U.S. PATENT DOCUMENTS

| | | |
|---|---|---|
| 1,612,697 | 12/1926 | Cecil . |
| 3,352,303 | 11/1967 | Delaney . |
| 3,614,953 | 10/1971 | Moss . |
| 3,894,673 | 7/1975 | Lowder et al. . |
| 4,018,576 | 4/1977 | Lowder et al. . |
| 4,273,128 | 6/1981 | Lary . |
| 4,445,509 | 5/1984 | Auth . |
| 4,572,186 | 2/1986 | Gould . |
| 4,589,412 * | 5/1986 | Kensey ................................ 606/159 |
| 4,631,052 | 12/1986 | Kensey . |
| 4,646,736 | 3/1987 | Auth . |
| 4,650,466 | 3/1987 | Luther . |
| 4,653,496 | 3/1987 | Bundy et al. . |
| 4,679,557 | 7/1987 | Opie et al. . |
| 4,685,458 | 8/1987 | Leckrone . |
| 4,696,667 | 9/1987 | Masch . |
| 4,728,319 | 3/1988 | Masch . |
| 4,732,154 | 3/1988 | Shiber . |
| 4,747,821 | 5/1988 | Kensey et al. . |
| 4,765,332 | 8/1988 | Fischell et al. . |
| 4,771,774 | 9/1988 | Simpson et al. . |
| 4,781,186 | 11/1988 | Simpson et al. . |
| 4,784,636 | 11/1988 | Rydell . |
| 4,794,928 | 1/1989 | Kletschka . |
| 4,794,931 | 1/1989 | Yock . |
| 4,857,045 | 8/1989 | Rydell . |
| 4,885,003 | 12/1989 | Hillstead . |
| 4,886,061 | 12/1989 | Fischell et al. . |
| 4,895,560 | 1/1990 | Papantonakos . |
| 4,921,484 | 5/1990 | Hillstead . |
| 4,926,858 | 5/1990 | Gifford, III et al. . |
| 4,950,238 | 8/1990 | Sullivan . |
| 4,966,604 | 10/1990 | Reiss . |
| 4,990,134 | 2/1991 | Auth . |
| 4,994,067 | 2/1991 | Summers . |
| 5,030,201 | 7/1991 | Palestrant . |
| 5,034,001 | 7/1991 | Garrison et al. . |
| 5,100,425 | 3/1992 | Fischell et al. . |
| 5,116,350 | 5/1992 | Stevens . |
| 5,135,483 | 8/1992 | Wagner et al. . |
| 5,135,531 | 8/1992 | Shiber . |
| 5,154,724 | 10/1992 | Andrews . |
| 5,176,693 | 1/1993 | Pannek, Jr. . |
| 5,217,474 | 6/1993 | Zacca et al. . |
| 5,224,945 | 7/1993 | Pannek, Jr. . |
| 5,250,060 | 10/1993 | Carbo et al. . |
| 5,286,253 | 2/1994 | Fucci . |
| 5,308,354 | 5/1994 | Zacca et al. . |
| 5,314,407 | 5/1994 | Auth et al. . |
| 5,314,438 * | 5/1994 | Shturman ................................ 606/159 |
| 5,318,576 | 6/1994 | Palssche Jr. et al. . |
| 5,395,311 | 3/1995 | Andrews . |
| 5,438,630 | 8/1995 | Daniel et al. . |
| 5,490,859 | 2/1996 | Mische et al. . |
| 5,501,694 | 3/1996 | Ressemann et al. . |
| 5,569,276 | 10/1996 | Jang et al. . |
| 5,649,941 | 7/1997 | Lary . |
| 5,653,696 | 8/1997 | Shiber . |
| 5,681,336 * | 10/1997 | Clement et al. ................ 606/159 |
| 5,725,568 | 3/1998 | Hastings . |
| 5,749,914 | 5/1998 | Janssen . |
| 5,766,192 | 6/1998 | Zacca . |
| 5,816,923 | 10/1998 | Milo et al. . |
| 5,842,479 | 12/1998 | Plaia et al. . |
| B1 4,842,579 | 10/1995 | Shiber . |
| B1 4,990,134 | 11/1996 | Auth . |

\* cited by examiner

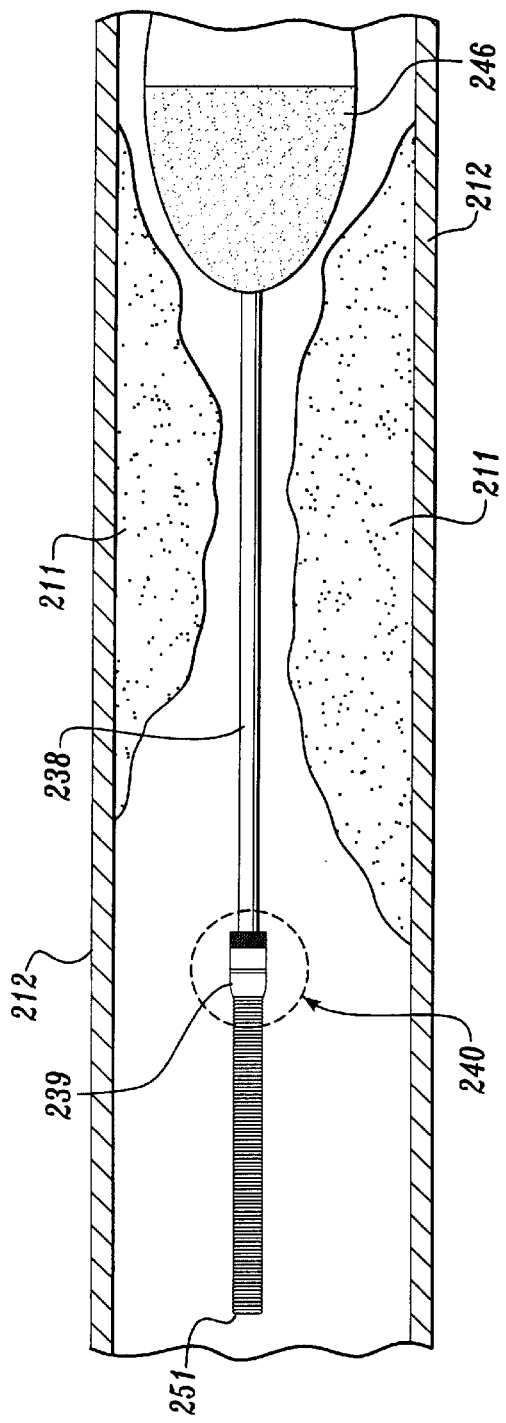
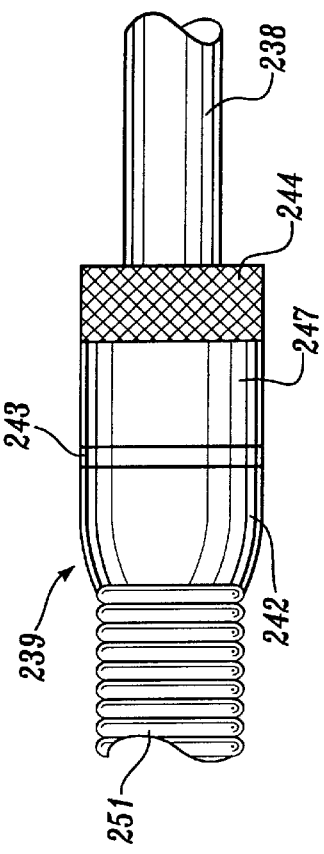
Fig. 22.
Fig. 23.

ABLATION DEVICE FOR REDUCING DAMAGE TO VESSELS AND/OR IN-VIVO STENTS

CROSS REFERENCE TO APPLICATIONS

The present invention is a continuation-in-part of U.S. patent application Ser. No. 09/035,734, filed Mar. 5, 1998, now U.S. Pat. No. 6,015,420 which is a continuation in part of U.S. patent application Ser. No. 08/813,827 and U.S. patent application Ser. No. 08/812,715, both filed on Mar. 6, 1997 both abandoned.

FIELD OF THE INVENTION

The present invention generally relates to devices for removing undesirable deposits from the lumen of a blood vessel or of a stent positioned in a blood vessel, and more particularly, to atherectomy devices.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. Vascular diseases, for example, may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. While a number of effective invasive therapies are available, it is desired to develop non-invasive therapies as well. Non-invasive therapies may be more desirable because of the possibility of decreased chances of infection, reduced post-operative pain, and less post-operative rehabilitation. Drug therapy is one type of non-invasive therapy developed for treating vascular diseases. Clot-dissolving drugs have been employed to help break up blood clots which may be blocking a particular vascular lumen. Other drug therapies are also available. Further, non-invasive intravascular treatments exist that are not only pharmaceutical, but also physically revascularize lumens. Two examples of such intravascular therapies are balloon angioplasty and atherectomy, both of which physically revascularize a portion of a patient's vasculature.

Balloon angioplasty is a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and is then inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It should be recognized that this procedure does not remove the matter from the patient's vasculature, but displaces and reforms it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus may not be prone or susceptible to angio-plastic treatment. Even if angioplasty is successful, there is a chance that the occlusion may recur. Recurrence of an occlusion may require repeated or alternative treatments given at the same intravascular site.

A relatively new technique to reduce the recurrence of occlusion after a balloon angioplasty procedure involves providing a stent at the revascularized site. A stent is typically a hollow tube, typically braided, that can be inserted into the vascular of a patient in a compressed form. Once properly positioned at a desired site, the stent is expanded to hold the vessel open in an attempt to prevent restenosis. While this technique can help maintain blood flow past the site, it has been found that the occluding material often migrates through the interstices of the stent braid, and may again occlude the vessel. This phenomenon is sometimes referred to as interstitial hyperplasia.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty, drug and/or stent therapies.

One such alternative mechanical treatment method involves removal, not displacement of the material occluding a vascular lumen. Such treatment devices, sometimes referred to as atherectomy devices, use a variety of material removal means, such as rotating cutters or ablaters for example, to remove the occluding material. (The term "atherectomy device" as used throughout the specification refers to ablation devices for use in any portion of a patient's vasculature. Thus, while the atherectomy devices provided in accordance with preferred embodiments of the present invention are well suited for use in the coronary arteries, their use is not limited to the coronary arteries.) The material removal device is typically rotated via a drive shaft that extends out of the vascular of the patient and to an electric motor.

In operation, an atherectomy device is typically advanced over a guide wire placed in vivo until the material removal device is positioned just proximal to the occluded site. The motor is used to rotate the drive shaft and the material removal device, and the material removal device is moved through the occluded vessel. The material removal device removes the material from the vessel, rather than merely displacing or reforming the material as in a balloon angioplasty procedure.

A potentially negative characteristic for all atherectomy devices is the unwanted perforation of a vessel wall by the material removal device. This can occur when the material removal device improperly engages the vessel wall, for example when the material removal device is not oriented substantially parallel to the axis of the vessel. In this situation, the material removal device (e.g., cutter or abrasive ablater) may improperly engage the vessel wall and cause unwanted damage thereto.

Similarly, an atherectomy device may cause damage to an in vivo stent when used to remove occluding material from within the stent caused by, for example, interstitial hyperplasia. Even a properly oriented material removal device may damage a stent. If the cutter or ablater of a typical atherectomy device engages a stent, particulates of the stent and/or material removal device may be removed and introduced into the vasculature of the patient, which can cause complications. To reduce this risk, the material removal device typically has an outer diameter that is substantially less than the inner diameter of the stent. It is believed that this may reduce the risk that the material removal device will engage and thus damage, the stent. A limitation of this approach is that a substantial gap typically must be provided between the material removal device and the stent. This may reduce the amount of occluding material that can be removed from within the stent. Accordingly, the stent will likely become occluded again sooner than if the outer diameter of the material removal device could more closely match the inner diameter of the stent, and remove more of the occluding material.

Given the above-discussed considerations, it would be desirable to provide an atherectomy device that can reduce the risk of damage to a vessel wall and/or an in vivo stent. In particular, it would be advantageous to provide an atherectomy device that can align the burr cutting action with a path through the stenosed vessel while removing unwanted material and yet not cause excessive wear on the vessel walls. The present invention fulfills these needs, and provides further related advantages.

SUMMARY OF THE INVENTION

The present invention overcomes many of the disadvantages of the prior art by providing an atherectomy device that may reduce the risk of damage to a vessel wall and/or an in vivo stent. In one embodiment of the present invention, an atherectomy device is provided that has a rotatable ablation burr attached to the distal end of a flexible drive shaft. The ablation burr can have generally elliptical proximal and distal shoulders and a generally cylindrical material removal portion therebetween. In a preferred embodiment, the material removal portion is substantially cylindrical and is recessed relative to the shoulders. In a preferred embodiment, the material removal portion contains abrasive material such as diamond grit adhered to the outer surface.

The proximal and distal shoulders are substantially less abrasive than the material removal portion. The shoulders are tapered and act to align the burr along a path through the stenosed vessel. Aligning the burr allows an unwanted, projecting deposit to be presented to the material removal portion while the less abrasive shoulders are presented to the vessel wall. The shoulders can serve to re-align the burr when the burr assumes a cant due to a tortuous path through a stenosed vessel.

In another embodiment of the present invention, an atherectomy device is provided that has a flexible drive shaft with an ablation burr attached to the distal end thereof. The ablation burr is preferably generally elliptical in shape except for a concave shaped leading surface. An abrasive grit is then disposed on the concave shaped leading surface. Extending distally from the concave shaped leading surface is a distal tip portion, and extending proximally from the concave shaped leading surface is a convex shaped portion. Both the distal tip portion and the convex shaped portion have non-abrasive surfaces.

In this configuration, the abrasive grit is effectively prevented from engaging a vessel wall regardless of the orientation of the ablation burr within the vessel. That is, the non-abrasive surfaces of the distal tip and the convex shaped portion will tend to engage the vessel wall before the concave shaped leading surface, and may effectively prevent the abrasive grit of the concave shaped leading surface from engaging the vessel wall. To further reduce the friction between the ablation burr and the vessel wall, the convex shaped portion may have a number of dimples formed therein.

It is recognized that the benefits of this embodiment may equally apply when the ablation burr is used to remove unwanted deposits from within a stent (e.g., interstitial hyperplasia). In this application, however, the present invention may effectively prevent the abrasive grit on the concave shaped leading surface from engaging the stent, rather than the interstitial hyperplasia. This may reduce the risk of damage to the stent.

In another embodiment of the present invention, the ablation burr may include an outer surface which is generally non-abrasive, but has a number of depressions therein forming a number of depressed surfaces. An abrasive is provided only on the depressed surfaces. In this configuration, all of the abrasive is positioned just below the outer surface of the ablation burr. Accordingly, only the non-abrasive outer surface of the ablation burr contacts the stent. The occluding material within the stent, however, may enter the depressions and become ablated. Preferably, the depressions form a number of depressed flutes in the outer surface of the ablation burr.

In another embodiment of the present invention, the ablation burr has a generally elliptical outer surface with a selected portion of the outer surface having an abrasive coating. The abrasive coating is formed from a material that is softer than the material used to form the stent. Accordingly, the abrasive may not damage the stent. In a preferred embodiment, the abrasive includes a number of chips or a grit that comprises plastic or some other malleable material that is softer than the material used to form the stent. It is known that stents are typically formed from stainless steel or Nitinol.

In another embodiment of the present invention, the atherectomy device includes a cutter device rather than an ablation device on distal end thereof. The cutter device may be generally elliptical in shape, and may have a number of cutter blades on at least a leading surface thereof. In this embodiment, at least a portion of selected cutter blades are made from a material that is softer than the material used to form the stent. As indicated above, stents are typically made from either stainless steel or Nitinol. In the present embodiment, it is contemplated that the cutter blades can be made from a softer material such as aluminum, titanium or annealed stainless steel. These materials are advantageous in that they are very ductile. It is contemplated, however, that the cutting blades may be surface hardened by oxidizing, nitriding, carbonizing or by some other process to maintain a sharp cutting edge. A sharp cutting edge is often important to minimize the particle size of the ablated atheroma. If the burr contacts the stent, the underlying ductile burr material preferably plastically deforms, thus preventing particle generation from either the burr or the stent.

An advantage of all of these embodiments is that the material removal device (e.g., cutter or ablater) can have an outer diameter that more closely matches the inner diameter of a stent. In prior atherectomy devices, the material removal device typically had an outer diameter that was substantially less than the inner diameter of the stent to reduce the risk that the material removal device will engage, and thus damage, the stent. However, in the present invention, appropriate portions of the material removal devices are formed from a softer material than the stent. This may allow the material removal device to engage the stent without substantially damaging the stent. Accordingly, the present invention may allow the material removal device to have an outer diameter that more closely matches the inner diameter of the stent, which may allow the material removal to remove more of the occluding matter from the stent.

In another preferred embodiment of the present invention, the ablation device includes a burr having an inner circumferential rim at the distal end of the burr and an outer circumferential rim that is spaced longitudinally from the inner circumferential rim by a first distance. The outer circumferential rim defines a maximum diameter of the burr. A leading surface extends between the inner and outer circumferential rims in a substantially uniform, concave manner. An abrasive is provided on the leading surface, and the burr is coupled to a drive shaft that selectively rotates the burr. Furthermore, the outer circumferential rim is preferably non-abrasive and is convex in profile.

In another embodiment of the present invention, a wire extends co-axially through the burr, such that a first distal end of the wire extends out of the body, distal to the first annular edge. An abrasive tip is coupled to a distal end of the wire and is selectively rotated to ablate unwanted deposits.

In another embodiment of the present invention, the burr is made of a compressible, elastomeric material. The burr is positioned in a compressed condition within a guide catheter for positioning at a desired location within a patient's vasculature. Once the guide catheter is at the desired location, the burr is pushed out of the catheter, allowing it to expand to a operational expanded condition.

In another embodiment to the present invention, an ablation device is advanced to a desired site within a patient's vasculature over a guide wire having a bearing provided at a distal region of the guide wire. The bearing has a dynamic member that acts as a bumper and rotates when the ablation device is advanced to the distal region of the guide wire and contacts the dynamic member. The guide wire having the bearing is advanced through the patient's vasculature until the bearing is positioned just distal of the unwanted deposit or lesion.

In another embodiment of the invention, an atherectomy burr having a relatively flat leading surface includes one or more aspiration ports through which particles ablated from a patient's vessel may be removed. The burr is driven with a substantially sealed drive shaft that may include a section of heat shrink tubing sandwiched between filar windings. The proximal end of the sealed drive shaft is connected to a regular atherectomy drive shaft through a coupling. The coupling includes a window that rotates with the burr. Surrounding the conventional drive shaft and coupling is a sheath. The proximal end of the sheath is connected to a source of vacuum that draws particles aspirated from the patient through the front face of the burr, the sealed drive shaft and through the window of the coupling. The particles then are drawn along the lumen of the shaft to a filter that is in line with the source of vacuum.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 22 illustrates a guide wire having a bearing position at its distal end disposed within a lumen according to another aspect of the present invention;

FIG. 23 is an enlarged side elevational view of the bearing illustrated in FIG. 22.

DETAILED DESCRIPTION OF THE INVENTION

Figure 1:
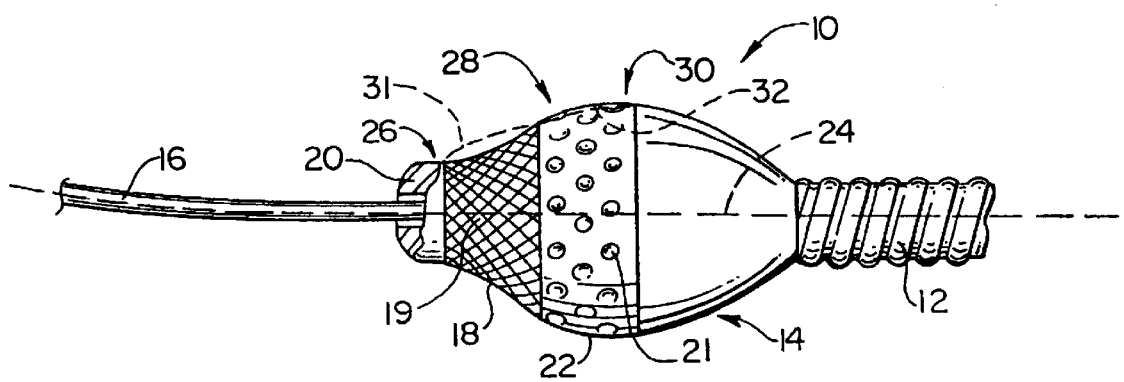
FIG. 1 is a side elevational view of an atherectomy device in accordance with a first embodiment of the present invention, including a concave shaped leading surface.

FIG. 1 is a side elevational view of an atherectomy device in accordance with a first embodiment of the present invention. The atherectomy device is generally shown at 10, and includes a flexible drive shaft 12 and an ablation burr 14. The flexible drive shaft 12 and ablation burr 14 have a lumen extending therethrough to receive a guide wire 16, as shown. In operation, the guide wire 16 is percutaneously inserted through the vasculature of a patient, and past the desired occlusion site. The atherectomy device 10 is then slid over the guide wire 16 until the ablation burr 14 is positioned just proximal to the occlusion site. A guide catheter may be used to assist in the positioning of both the guide wire 16 and the atherectomy device 10, as is known in the art. The proximal end of the drive shaft remains outside the body and is attached to an electric motor. The motor rotates the atherectomy device while the atherectomy device is advanced distally through the occlusion site. The ablation burr 14 removes the occluding material by ablation.

Preferably, the atherectomy device 10 comprises a flexible drive shaft 12 attached to an ablation burr 14, wherein the flexible drive shaft 12 and the ablation burr 14 are disposed about a central axis 24. The ablation burr 14 has a first cross section 26 spaced from a second cross section 28, wherein the second cross section 28 has a larger cross sectional area than the first cross section 26. The ablation burr 14 further has a first outer surface 18 that extends between the first cross section 26 and the second cross section 28, and extends inward toward the central axis 24 relative to an imaginary line 31 that extends between the first cross section 26 and the second cross section 28 as shown.

The atherectomy device 10 may further have a third cross section 30 spaced relative to the second cross section 28, wherein the ablation burr 14 includes a second outer surface 22 that extends between the second cross section 28 and the third cross section 30. The second outer surface 22 extends outward away from the central axis 24 relative to an imaginary line 32 that extends between the second cross section 28 and the third cross section 30.

More specifically, and in a preferred configuration, the ablation burr 14 is generally elliptical in shape, except for a concave shaped leading surface 18 as shown. An abrasive grit 19, shown in a cross hatch, is disposed on the concave shaped leading, surface 18. The abrasive grit may be a diamond grit. Extending distally from the concave shaped leading surface 18 is a distal tip portion 20, and extending proximally from the concave shaped leading surface 18 is a convex shaped portion 22. Both the distal tip portion 20 and the convex shaped portion 22 preferably have non-abrasive surfaces. In this configuration, the abrasive grit 19 is effectively prevented from engaging a vessel wall regardless of the orientation of the ablation burr 14 within a vessel. This is shown and described in more detail with reference to FIG. 2.

Figure 2:
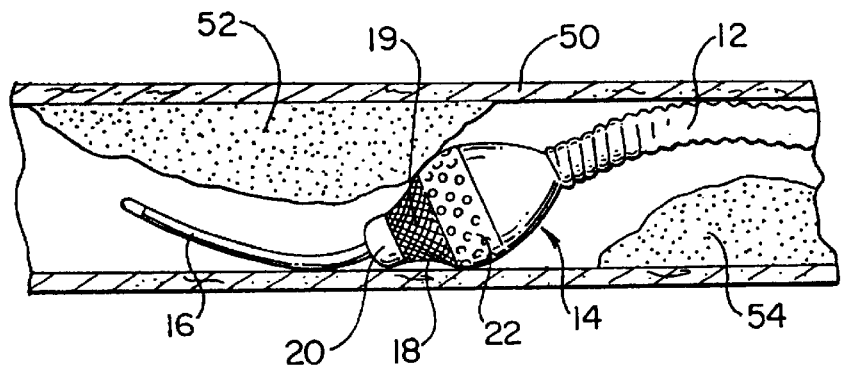
FIG. 2 is a side elevational view of the embodiment shown in FIG. 1 ablating an occluded vessel.

FIG. 2 shows a vascular lumen 50 having occlusion material 52 and 54 disposed therein. To traverse the vascular lumen 50, the guide wire 16 may have to assume an "S" shape as shown. This configuration may cause the ablation burr 14 to be oriented at an angle relative to the central axis of the vascular lumen 50. When this occurs, the non-abrasive surfaces of the distal tip 20 and the convex shaped portion 22 will tend to engage the wall of the vessel 50 before the concave shaped leading surface 18, and may effectively prevent the abrasive grit 19 from engaging the vessel wall. Preferably, the convex shaped portion 22 has a number of dimples 21 formed therein to reduce the friction between the ablation burr 14 and the wall of the vessel 50.

It is recognized that the ablation burr 14 may become offset from the central axis of a lumen for a number of reasons, and the above example is only illustrative. Another illustrative example is when the atherectomy device 10 is substantially less flexible than the guide wire 16, which is usually the case. In this situation, and when a relatively sharp bend in the vascular lumen is encountered, the atherectomy device may tend to bend the guide wire toward a vessel wall. This may cause the ablation burr 14 to improperly engage the vessel wall.

Figure 3:
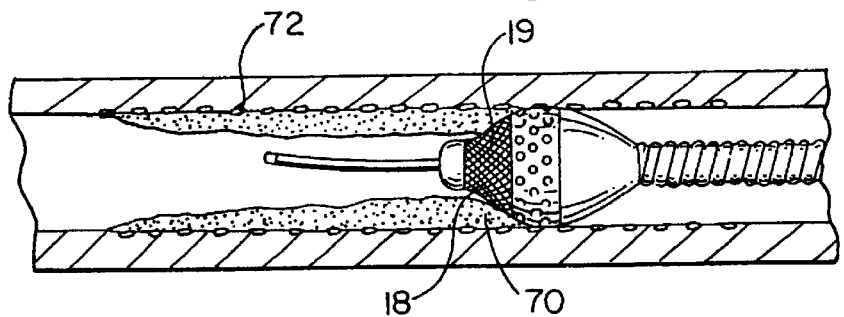
FIG. 3 is a side elevational view of the embodiment shown in FIG. 1 ablating an occluded stent.

FIG. 3 is a side elevational view of the embodiment shown in FIG. 1 ablating an occluded stent. It is recognized that the benefits of the embodiment shown in FIG. 1 may equally apply when the ablation burr is used to remove unwanted deposits (e.g., interstitial hyperplasia) 70 from within a stent 72. In this application, however, the present invention may effectively prevent the abrasive grit 19 on the concave shaped leading surface 18 from engaging the stent 72, rather than the vessel wall. This may reduce the risk that the ablating burr 14 will damage the stent 72. Accordingly, the ablating burr 14 may have an outer diameter that more closely matches the inner diameter of the stent 72.

Finally, it is contemplated that the material used to form the distal tip 20 and the convex shaped portion 22 may be softer than the material used to form the stent 72. This may further reduce the chance that the ablating burr 14 will damage the stent 72.

Figure 4:
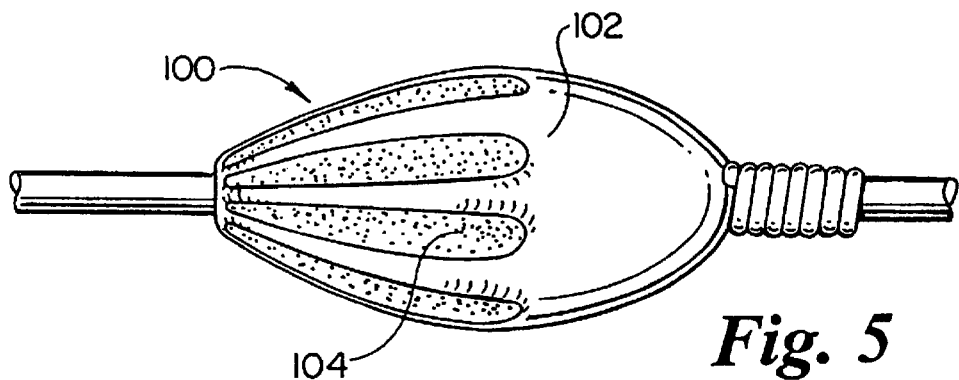
FIG. 4 is a side elevational view of an atherectomy device in accordance with another embodiment of the present invention, including a number of fluted depressions in the outer surface of the ablating burr.
Figure 5:
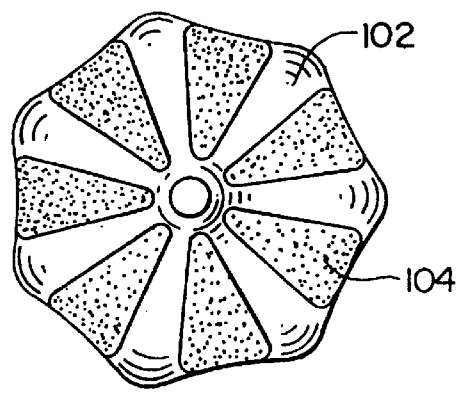
FIG. 5 is a front view of the embodiment shown in FIG. 4.

FIG. 4 is a side elevational view of an atherectomy device in accordance with another embodiment of the present invention, including a number of fluted depressions in the outer surface of the ablating burr. FIG. 5 is a front view of the embodiment shown in FIG. 4. In this embodiment, the ablation burr 100 includes an outer surface 102 which is generally non-abrasive, and a number of depressions 104 formed therein. Each of the number of depressions 104 form a depressed surface. An abrasive is provided on each of the depressed surfaces as shown, such that the abrasive is located just below the outer surface 102 of the ablation burr 100. In this configuration, only the non-abrasive outer surface 102 of the ablation burr 100 contacts the stent, and the occluding material within the stent enters the depressions 104 and becomes ablated. Preferably, the abrasive is a diamond grit, and the number of depressions 104 form a number of depressed flutes in the outer surface 102 of the ablation burr 100, as shown.

Figure 6:
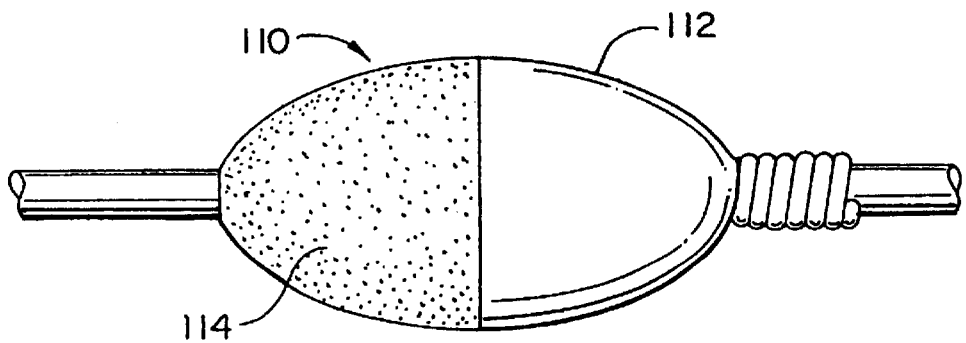
FIG. 6 is a side perspective view of another embodiment of the present invention, including an abrasive outer surface that is formed from a material that is softer than the material used to form the stent.

In another embodiment of the present invention, and as shown in FIG. 6, the ablation burr 110 has a generally elliptical outer surface 112 with a selected portion of the outer surface 114 covered with an abrasive. Preferably, the abrasive 114 is applied to either the entire outer surface 112 or to just the leading half of the outer surface 112.

In accordance with the present invention, the abrasive surface 114 is formed from a material that is softer than the material used to form the stent. Thus, the abrasive may not damage the stent if the material removal device engages the stent. Preferably, the abrasive comprises a number of chips or a grit of plastic or some malleable material which is softer than the material used to form the stent. It is known that stents are typically formed from stainless steel or Nitinol.

Figure 7:
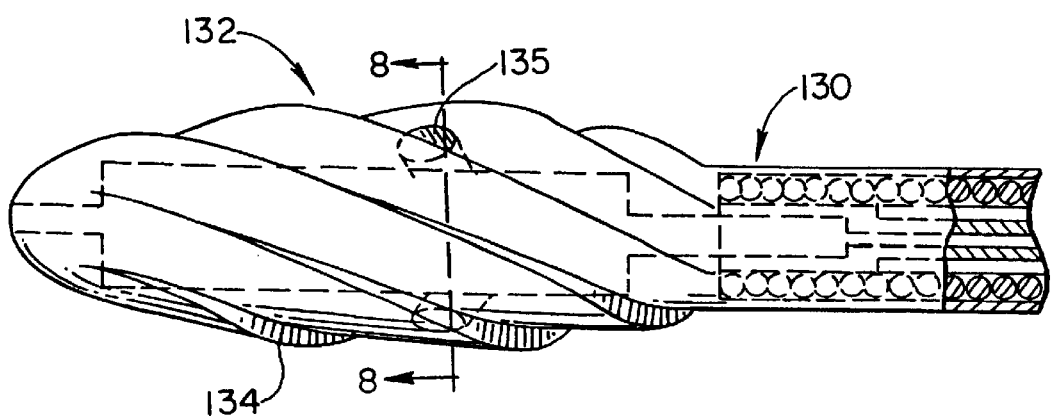
FIG. 7 is a partial cross sectional view of another embodiment of the present invention including a number of cutter blades.
Figure 8:
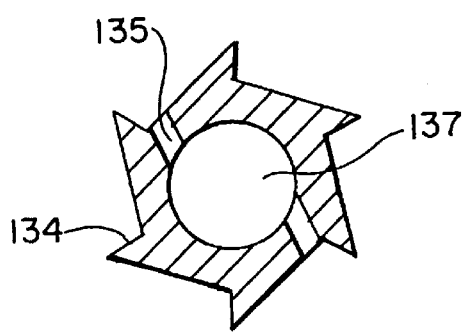
FIG. 8 is a cross-sectional side view taken along lines 8—8 of FIG. 7.

In another embodiment, and as shown in FIG. 7, the atherectomy device includes a cutter device 132 rather than an ablation device as described above. FIG. 8 is a cross-sectional side view taken along lines 8—8 of FIG. 7. The cutter device 132 may be generally elliptical in shape as shown, and may have a number of cutter blades 134 on the outer surface thereof. In accordance with the present invention, at least a portion of the cutter blades 134 are made from a material that is softer than the material used to form the stent. As indicated above, stents are typically made from either stainless steel or Nitinol. In the present embodiment, it is contemplated that selected portions of the cutter blades 134 are made from a softer material such as aluminum (e.g., an aluminum alloy 1060-0), pure titanium or annealed stainless steel. These materials are advantageous in that they are very ductile. It is contemplated, however, that the cutting blades 134 may be hardened by oxidizing, nitriding, carbonizing or by some other process to maintain a sharp cutting edge. A sharp cutting edge is often important to minimize the particle size of the ablated atheroma. If the burr contacts the stent, the underlying ductile burr material preferably plastically deforms, thus preventing particle generation from either the burr or the stent.

In the illustrative embodiment, holes 135 connect the outside of the burr (cutting surface) to the inner guide wire lumen 137. The holes 135 may be spaced at any angular interval around the diameter of the burr and at multiple points along the length of the burr. For optimum performance, the holes are preferably angled relative to an axis that is perpendicular to the central axis of the burr, as shown.

The holes 135 preferably perform one or more tasks. For example, the holes 135 may aspirate the ablated material when a vacuum is applied to the inner guide wire lumen 137. Aspiration of the ablated material may help keep the ablated particulate from being embolized distally of the ablation site. Alternatively, the holes 135 may infuse fluid to the ablation site. The infusion of fluids may help cool the site (and thus help prevent restenosis) and/or may help lubricate the ablation site to make it more difficult to unintentionally cut a vessel wall or ablate a stent.

Figure 9:
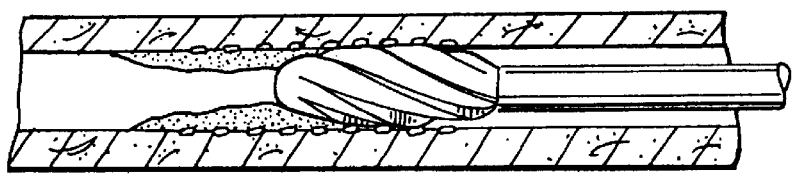
FIG. 9 is a side elevational view of the embodiment shown in FIG. 7 cutting through an occluded stent.

FIG. 9 is a side elevational view of the embodiment shown in FIG. 7 cutting through an occluded stent. Because the cutter blades 134 are made from a material that is softer than the material used to form the stent, the outer diameter of the cutter device 132 may more closely match the inner diameter of the stent. This is an advantage of all of the above embodiments. That is, in prior atherectomy devices, the material removal device typically had an outer diameter that was substantially less than the inner diameter of the stent to reduce the risk that the material removal device will engage, and thus damage, the stent. In the present invention, however, appropriate portions of the material removal devices (e.g., ablaters or cutters) may be formed from a softer material than the stent, which may protect the stent. In addition, the abrasive surfaces may be designed to not engage the stent. Accordingly, the material removal device may have an outer diameter that more closely matches the inner diameter of the stent, which may allow the material removal device to remove more of the occluding matter from within the stent.

Figure 10:
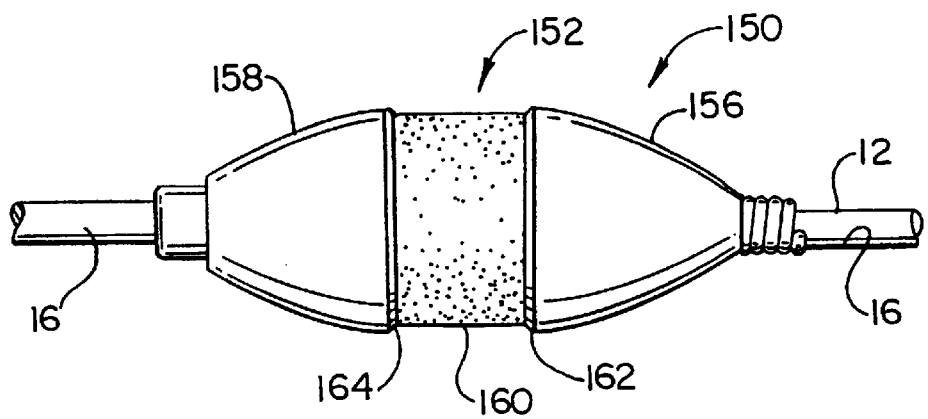
FIG. 10 is a fragmentary, side, perspective view of an atherectomy device having a guide wire disposed therethrough.

Referring now to FIG. 10, an atherectomy device 150 is illustrated, having an atherectomy burr 152 for removing unwanted material. Burr 152 includes a proximal shoulder 156, a distal shoulder 158, and is secured to the distal end of flexible drive shaft 12. Drive shaft 12 and burr 152 have a lumen therethrough, allowing passage of guide wire 16. An intermediate material removal portion 160 lies between proximal shoulder 156 and distal shoulder 158. In the preferred embodiment, illustrated in FIG. 10, material removal portion 160 is abrasive. One embodiment contains abrasive grit secured to the burr outer surface. Another embodiment includes abrasive chips fixed to the outer surface. A preferred abrasive material includes diamonds. Yet another embodiment includes cutting blades in the material removal portion.

In the embodiment illustrated, abrasive portion 160 is recessed relative to the proximal and distal shoulders, having a smaller radial extent and circumference than the maximum radial extent of either of the shoulders. In a preferred embodiment, transition portions lie between abrasive portion 160 and the distal and proximal shoulders. In the embodiment illustrated, a proximal transition portion 164 and a distal transition portion 162 lie between abrasive portion 160, and proximal shoulder 156 and distal shoulder 158, respectively. In one embodiment the transition portions have a straight taper while in another embodiment the transition portions have a rounded taper. In yet another embodiment, the transition portions are substantially larger, and can approach the size of the shoulders. In this embodiment, the larger transition portions impart a dumbbell appearance to the atherectomy burr.

Figure 11:
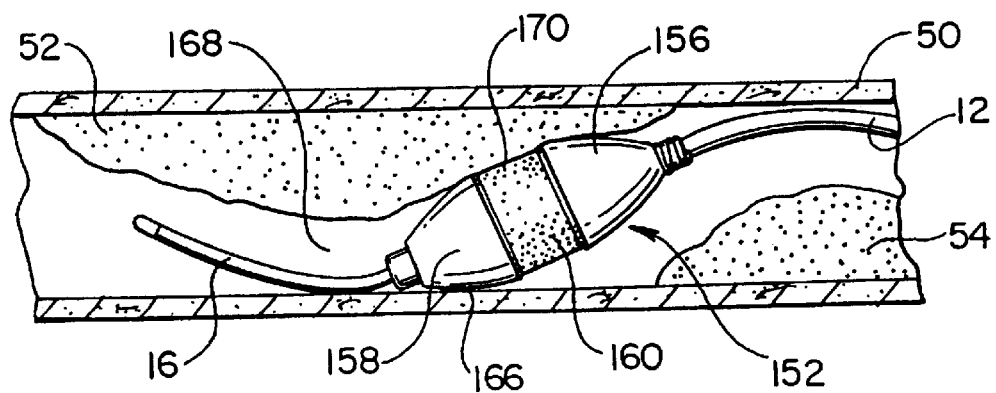
FIG. 11 is a fragmentary, side, perspective view of the atherectomy device disposed within a lumen having an asymmetrical lesion.

Referring now to FIG. 11, atherectomy device 150 is illustrated disposed within vessel 50 between a first deposit 52 and a second deposit 54. Deposits 52 and 54 are deposited on opposite sides of vessel 50, creating a tortuous path through the vessel. The path illustrated forces atherectomy burr 152 to can't relative to the vessel longitudinal axis, forcing distal shoulder 158 into contact with the wall of vessel 50 as indicated at 166. If distal shoulder region 166 was abrasive, the rotating, abrasive portion could be forced into contact with the vessel wall. If drive shaft 16 is pushed in a distal direction with sufficient force, it is also possible in some vessel geometries, to force proximal shoulder 156 into an opposite wall of the vessel as well.

As indicated at 170, abrasive portion 160 is brought to bear against deposit 52, allowing the unwanted material to be removed by the rotating atherectomy burr. At the same time, less abrasive distal shoulder 166 is presented to the wall of vessel 50. As burr 152 is advanced over guide wire 16, distal shoulder 166 will follow a path between the vessel wall and the deposit, and will present abrasive portion 160 to the deposit in region 168. At this location, distal shoulder 166 can act to align burr 152 with the path or channel between the deposit and the vessel wall. An inwardly projecting portion of deposit 52 will be presented to recessed, abrasive portion 160, while the smooth vessel wall will not substantially protrude into the recessed, abrasive portion. The deposit can be removed while the vessel wall remains untouched by the abrasive.

The cam action of the burr shoulders thus acts to align the abrasive or cutting action of the burr with the path through the vessel and deposits. The improved burr can reduce the wear on a vessel wall associated with cutting the corner of a bifurcated ostial lesion.

Figure 12:
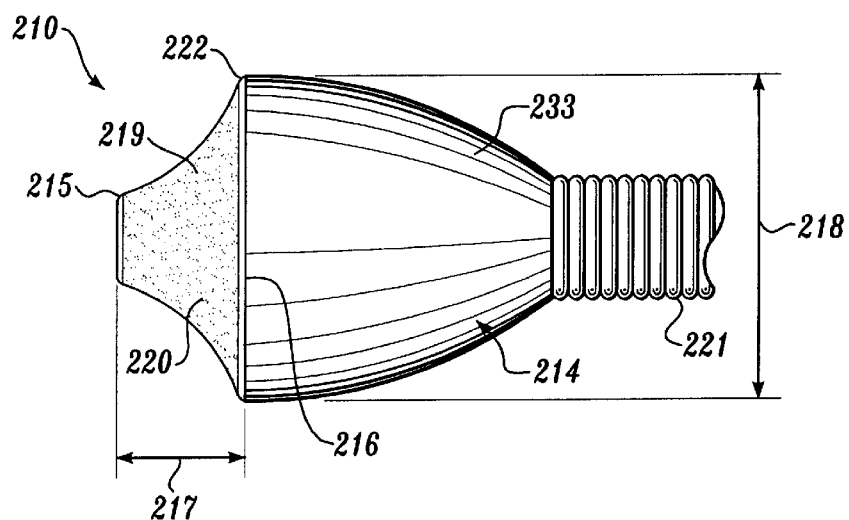
FIG. 12 is a side elevational view of a currently preferred embodiment of the atherectomy device including a concave shaped leading surface according to the present invention.

A currently preferred embodiment of the atherectomy device according to the present invention is illustrated in FIG. 12. The atherectomy device 210 includes an ablation burr 214 having a generally concave front or leading surface 219 and a generally ellipsoidal rear or trailing surface 233. The concave front surface is positioned between an inner, relatively smooth, circumferential rim 215 at the distal tip of the burr and an outer relatively smooth circumferential rim 216 that is positioned proximal to the inner circumferential rim 215. The diameter of the inner circumferential rim is preferably just larger than the diameter of a cylindrical lumen that extends through the burr for passage of a guide wire. The diameter of the outer circumferential rim 216 is preferably equal to the maximum diameter of the burr. The leading surface 219 of the burr is concave in cross section and is covered with an abrasive material 220, for example, diamond grit, to ablate an obstruction as the burr is rotated. Similar to the embodiments discussed previously, the burr is coupled to a drive shaft 221 that selectively rotates the burr at high speed.

The inner and outer circumferential rims 215, 216 are concentric, and are spaced longitudinally by a distance 217. The distance 217 is selected to adjust the pitch or "flatness" of the leading surface.

Figure 13:
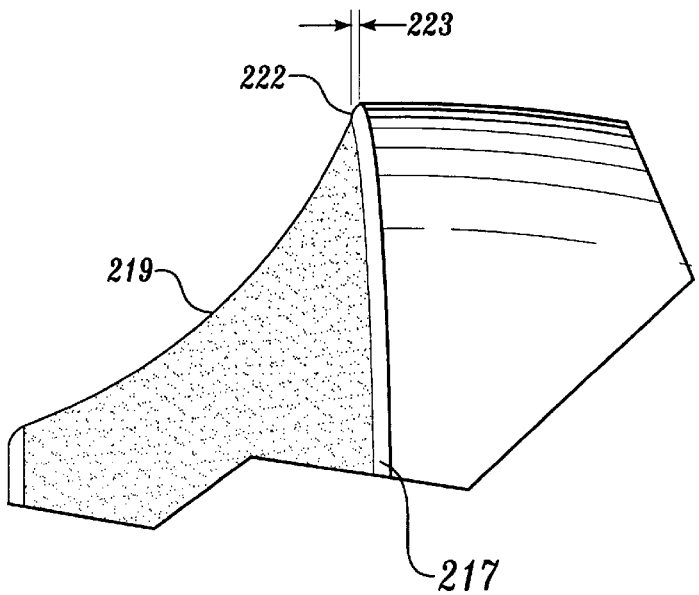
FIG. 13 is an enlarged view of a portion of the atherectomy device illustrated in FIG. 12.

In a currently preferred embodiment of the ablation burr, as illustrated in FIG. 13, the outer circumferential rim 216 includes a convex top surface 222. In a preferred embodiment, the outer circumferential rim has a width 223 of approximately 0.001–0.004 inches, and is preferably 0.002 inches wide.

It is believed that potential trauma to the artery or stent, and any potentially resulting complications, are minimized by providing an ablation device having the configuration illustrated in FIG. 12, given the smooth convex outer circumferential rim 216 and the shape and reduced surface area of the first leading surface 219. In particular, if the burr contacts the vessel wall, the area of contact between the abrasive and the vessel wall is reduced. It is further believed that given the proximity of the abrasive to a longitudinal axis of the burr, the speed of the movement of a majority of the abrasive surface is reduced for a given RPM. As a result, an ablation device provided in accordance with this presently preferred embodiment of the invention ablates a desirably sized lumen, while reducing hemolysis and platelet aggregation.

Figure 14:
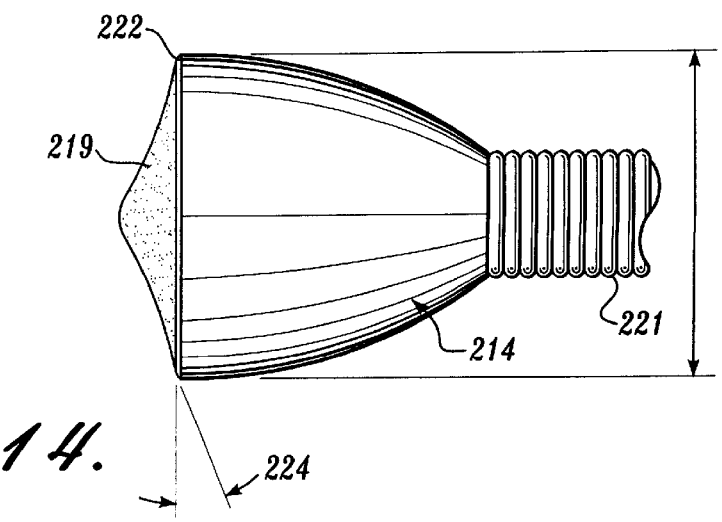
FIG. 14 is a side elevational view of an alternative embodiment of the atherectomy device according to the present invention.
Figure 15:
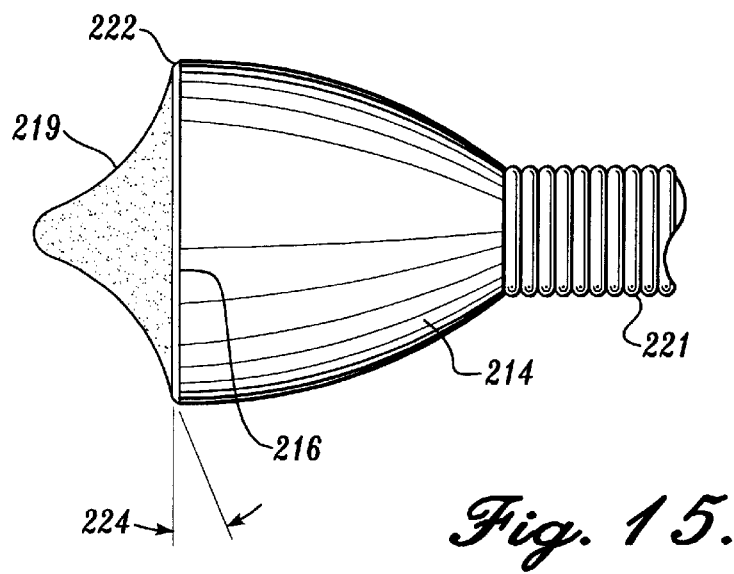
FIG. 15 is a side elevational view of another alternative embodiment of the atherectomy device according to the present invention.

It is further believed that an ablation device provided in accordance with this embodiment of the present invention reduces RPM drop inconsistency. When in use, the burr is spun at approximately 180,000 RPM. When the burr engages the lesion or unwanted deposits, the ablation process causes a drop of approximately 5,000 RPM. As will be understood by one of ordinary skill in the art, it is desirable to maintain a consistent RPM drop of 5,000 during ablation of the lesion. If an excessive RPM drop occurs, it is typically accompanied by increased torque and an undesirable increase in heat, as well as an increase in the quantity and size of particles generated by the ablation. It is believed that a more stable drop in RPM is achieved by reducing the abrasive surface area in contact with the lesion, and providing a steeper angle of contact with the lesion. As illustrated in FIGS. 14 and 15, the leading surface 219 is provided with a selected curvature such that the leading surface extends away from the outer circumferential rim 216 towards the inner circumferential rim 215 at a desired contact angle 224 measured relative to the outer circumferential rim 216. The steeper the contact angle, the less likely it is that the abrasive outer surface will contact the wall of the vessel or stent. It is also less likely that the abrasive will contact a vessel wall, when the burr is maneuvered around a corner. It is further believed that a steeper angle of contact and reduced abrasive surface area lessens the impact of side forces and potential vibrations that can result from fluctuations in the axial load applied by the operator.

Figure 16:
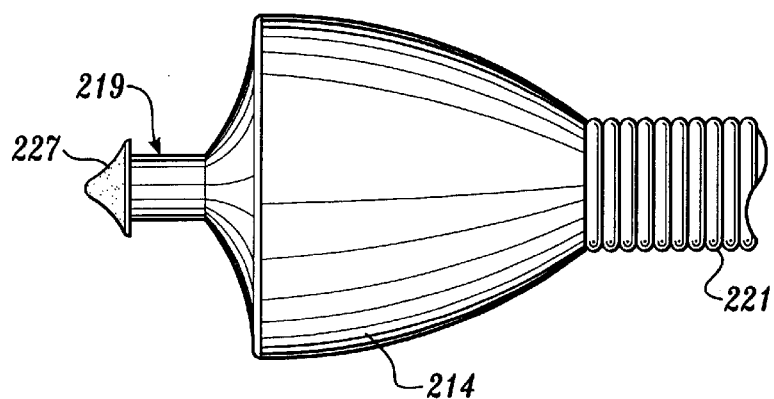
FIG. 16 is a side elevational view of another alternative embodiment of the atherectomy device according to the present invention, illustrating an ablative wire.
Figure 17:
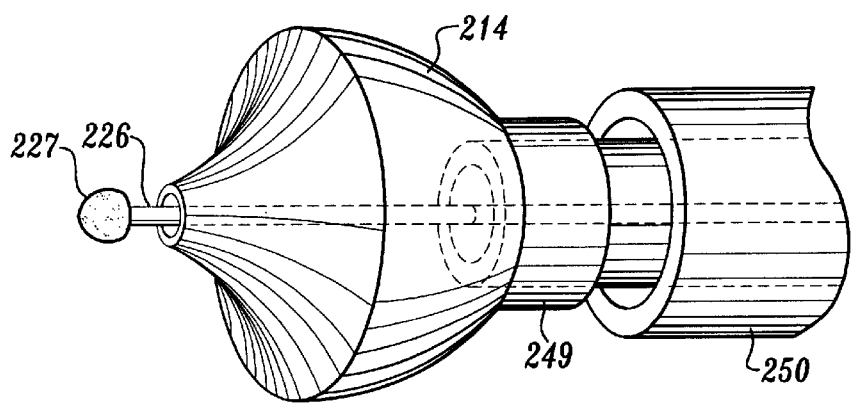
FIG. 17 is a front isometric view of another alternative embodiment of the atherectomy device according to the present invention.

In an alternative embodiment, illustrated in FIG. 16, a guide wire 225 extends co-axially through the burr. A distal end 226 of the wire extends out of the burr, distal to the inner circumferential rim 215. An abrasive tip 227 is coupled to the distal end of the wire. The wire may be keyed or coupled to the burr such that the wire and burr spin simultaneously, as illustrated in FIG. 16. Alternatively, as illustrated in FIG. 17, the guide wire 225 may be coupled to a motor (not shown) at a proximal end, which spins the wire independently of the burr. As further illustrated in FIG. 17, the burr 214 is coupled to a sheath 249 which in turn extends through an outer catheter sheath 250. The abrasive tip is made of a highly radiopaque material, allowing the device to be maneuvered using fluoroscopy, as is known in the art. In a preferred embodiment, the wire is spun at a rate of between 10,000–100,000 RPM. An ablation device provided in accordance with this embodiment may be particularly useful where the obstruction is extensive, making it difficult to pass a conventional guide wire through the obstruction. The tip 227 of the wire ablates the obstruction, helping to create a path for the burr. This embodiment provides the added benefit of working a wire across the lesion, such that if the vessel spasms and collapses, a path is available to facilitate the reopening of the vessel.

Figure 18:
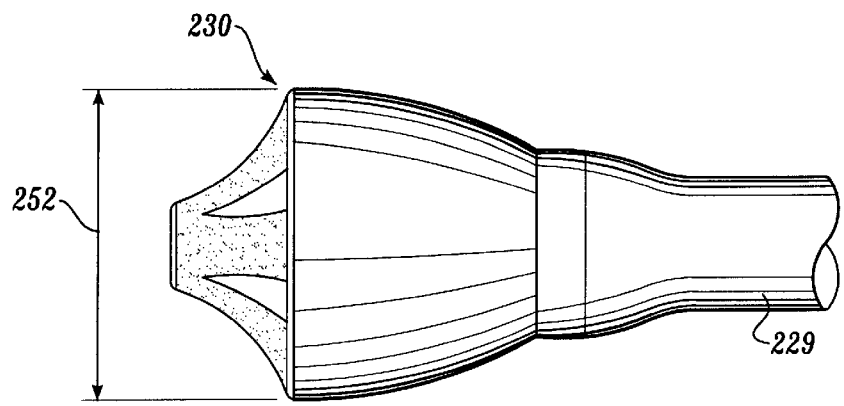
FIG. 18 is a side elevational view of an expandable atherectomy device having a concave leading surface according to another aspect of the present invention.
Figure 19:
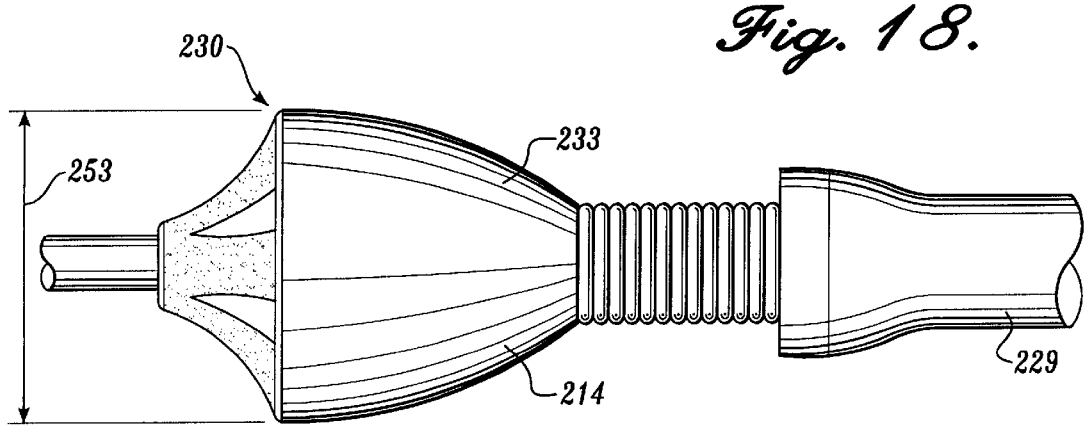
FIG. 19 is a side elevational view of the device illustrated in FIG. 18, in an expanded position.

In yet another embodiment of the ablation device illustrated in FIGS. 18 and 19, the burr 214 is made of a compressible, elastomeric material. The burr is positioned in a compressed condition 228 having a first diameter 252 within a guide catheter 229. Once the guide catheter is maneuvered through a patient's vasculature to a desired location, the burr is pushed out of the catheter, allowing the burr to expand to a second expanded condition 230 having a second diameter 253, as seen in FIG. 19. While a variety of materials may be used, the burr body may be made of a polymeric material such as urethane, or foam, or it may be hollow by providing a skin that is supported by one or more expandable ribs.

To facilitate the deployment of the burr from the catheter, a lubricant such as Bio-Slide is placed on at least a portion of the ellipsoidal trailing surface 233 that extends proximally from the second annular edge 216 to the drive shaft 221. In this manner, it is possible to reduce the width of the burr to facilitate placement, particularly when it is necessary to pass through narrow openings, such as the coronary ostia. For example, a catheter used to position the ablation device in the coronary ostia typically cannot exceed 8 French. When using conventional burrs, this would therefore limit the maximum diameter of the burr and resulting lumen to approximately 2 mm. However, by providing a burr in accordance with the present invention, the burr has a maximum diameter of 2 mm when positioned in the first compressed condition within the catheter, and expands to a diameter of 3 mm when deployed from the catheter. As a result, it is possible to create a 3 mm wide lumen in a single pass in a region where it was previously only possible to create a 2 mm lumen in a single pass.

Figure 20:
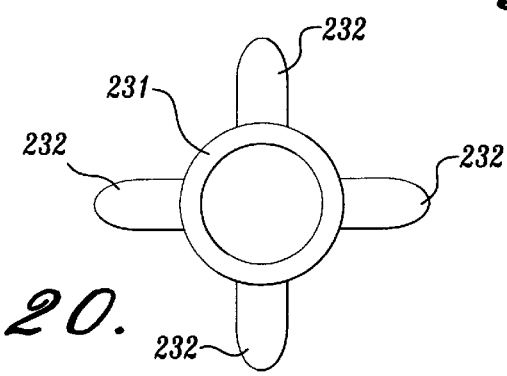
FIG. 20 is a top plan view of a joining mechanism used in the expandable atherectomy device illustrated in FIGS. 18 and 19.

In order to couple the polymeric material that comprises the body of the burr to the drive shaft, a pin 231 having a plurality of radially extending splines 232 is provided, as illustrated in FIG. 20. The elastomeric burr is cast over the splines, such that the splines mechanically grasp the elastomeric material. The pin 231 is coupled to the drive shaft, thereby coupling the elastomeric burr to the shaft.

Figure 21:
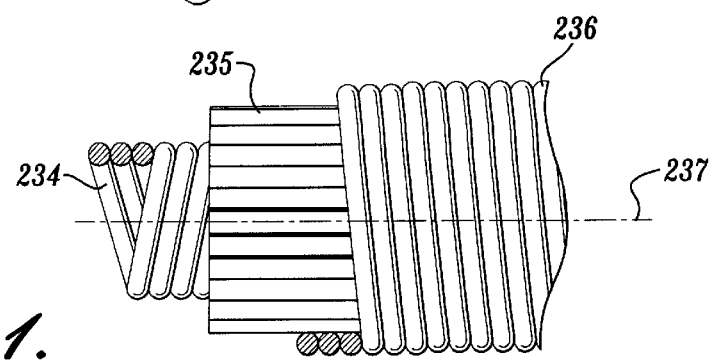
FIG. 21 is a side elevational view of a drive coil provided in accordance with yet another aspect of the present invention.

Although the drive shaft 221 may be made of a variety of materials, in a preferred embodiment, as illustrated in FIG. 21, the shaft is comprised of an inner coil 234, and outer coil 236, and a middle layer 234 provided between the inner and outer coils. In a preferred embodiment, the inner coil 234 is formed of a wire or strip wound in a first lay, the outer coil 236 is formed of a wire or strip wound in a second lay opposite that of the first lay, and the middle layer 235 is formed of a longitudinally rigid material. In a preferred embodiment, the middle layer is formed of a number of straight wires or strips, oriented parallel to a longitudinal axis 237 of the drive coil. Alternatively, the middle layer may be formed of heat shrink, thin walled hypotube, polymer tubing, or any other longitudinally rigid material. As a result, the drive shaft 221 maintains high bending flexibility while increasing its longitudinal stiffness.

In a preferred embodiment, an ablation device 246 is advanced to a desired site within a patient's vasculature over a guide wire 238. As illustrated in FIGS. 22 and 23, a bearing 239 is coupled to a distal region 240 of the guide wire. As best seen in FIG. 23, the bearing 239 has a static member 242 coupled to the guide wire which does not move, and a dynamic member 241 that is free to rotate over the guide wire and is separated from the static member by ball bearings 243. The dynamic member 241 acts as a bumper and rotates when the ablation device is advanced to the distal region of the guide wire and contacts the dynamic member 241. In a preferred embodiment, the guide wire 238 having a bearing 239 is advanced through the patient's vasculature 212 until the bearing 239 is positioned just distal of the unwanted deposit or lesion 211. Conventionally, when the ablation device works through the distal end of a lesion, the sudden lack of resistance results in the ablation device darting forward and engaging the spring tip 251 that is secured to the distal end of the guide wire. The friction caused by the rotating burr may generate sufficient heat to weld the burr to the spring tip 251 of the guide wire. By positioning a bearing 239 on the guide wire, and positioning the guide wire such that the bearing is located just distal of the lesion, darting and the associated problems are substantially eliminated. In a preferred embodiment, an outer surface 244 of the dynamic member 241 has a low durometer, to prevent the dynamic member from ablating the inner wall of the vessel or stent as it rotates.

Figure 24:
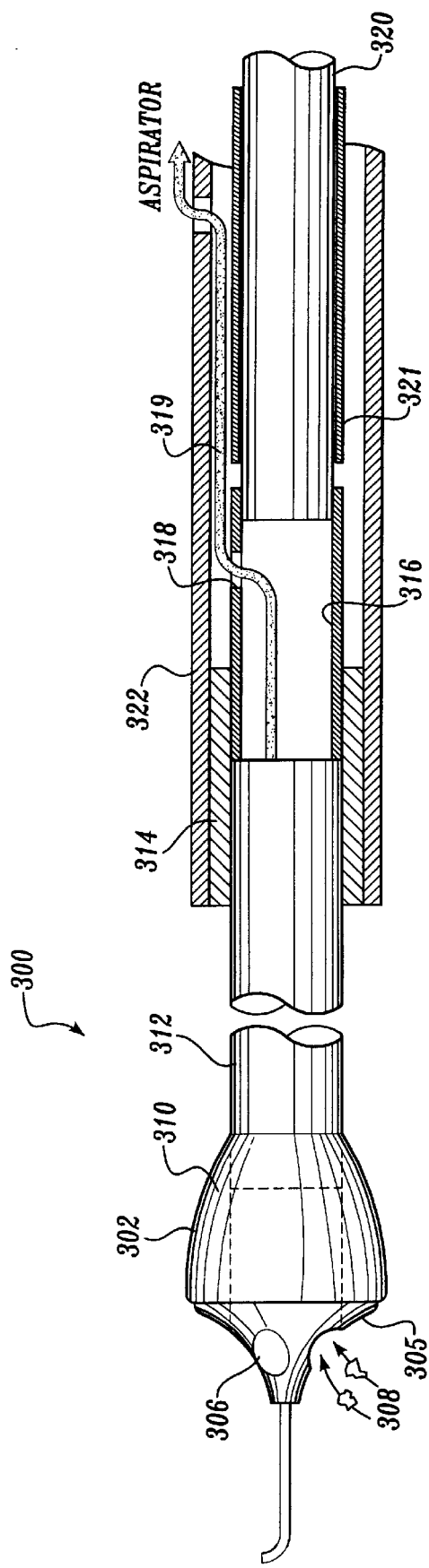
FIG. 24 illustrates an atherectomy burr including a number of aspiration ports on its leading surface according to another aspect of the invention.

FIG. 24 illustrates an atherectomy device according to yet another aspect of the present invention. The atherectomy device 300 includes an ablation burr 302 having a generally concave leading surface 304. An abrasive covers a portion of the leading surface in order to ablate an occlusion within a patient's blood vessel in the manner described above. The leading surface 304 includes one or more ports 306 through which aspirated particles 308 may be removed from the patient's blood vessel.

The burr 302 includes a proximal, central lumen 310 into which a sealed drive shaft 312 is fitted. A distal central lumen is provided for the passage of a guide wire. The drive shaft 312 generally comprises a length of heat shrink tubing or other non-permeable material sandwiched between two windings. The drive shaft 312 has a central lumen that is in fluid communication with the aspiration ports 306 on the leading surface of the burr. The proximal end of the sealed drive shaft 312 is connected to a coupler 314. A central portion 316 of the coupler 314 includes a window 318 through which fluid may be drawn. A conventional drive shaft 320 is secured at the proximal end of the coupler 314. A sheath 321 surrounds the driveshaft 320 such that a lubricating fluid can be injected between the sheath 321 and the driveshaft 320.

Surrounding the sheath 321 and coupler 314 is an outer sheath 322. The proximal end of the sheath 322 is connected to a vacuum source and a collection jar in series with the vacuum source. Particles removed from the patient's vessel therefore travel through the aspiration ports 306 on the leading surface of the burr, through the sealed drive shaft 312, out the window 318 and along a passage 319 contained between the inner diameter of the outer sheath 322 and the outer diameter of the sheath 321. The gap between the sheath 321 and the outer sheath 322 is sealed proximal to the point at which the outer sheath is coupled to the source of vacuum.

The placement of the aspiration ports 306 prevents their direct contact with healthy tissue. This feature coupled with the highly flexible sealed drive shaft may allow the device to be used in treating such diseases as Saphenous Vein Graft disease or other diseased having lesions with thrombus.

From the foregoing, it will be appreciated that although embodiments of the invention have been described herein for purposes of illustration, various modifications may be made without deviating from the spirit of the invention. It will also be understood that it is possible to use the various embodiments described herein in various combinations with each other. Thus, the present invention is not limited to the embodiment described herein, but rather is defined by the claims which follow.

The embodiments of the invention in which an exclusive property or privilege is claimed are defined as follows:

1. An atherectomy device comprising:
    a solid burr body having:
        a distal end and proximal end and a concave leading surface with a radius about a longitudinal axis of the burr body that increases from the distal end of the burr to a point that is proximal to the distal end;
        an abrasive on the concave leading surface; and
        one or more aspiration ports disposed on the concave leading surface of the burr;
    a substantially sealed drive shaft coupled to the burr, the scaled drive shaft including a lumen that is in fluid communication with the one or more aspiration ports on the leading surface of the burr, and
    a source of vacuum coupled to the sealed drive shaft to withdraw particles ablated from a patient's vessel as the burr is rotated.

2. The atherectomy device of claim 1, further comprising:
    a coupler into which the sealed drive shaft is fitted,
    a second drive shaft received in the coupler,
    a sleeve fitted over the second drive shaft and coupler,
    the coupler including a window through which particles drawn through one or more aspiration ports are passed.

3. The atherectomy device of claim 1, wherein the radius of the concave leading surface lies entirely below an imaginary line that extends between the distal end and the point proximal to the distal end.

* * * * *

UNITED STATES PATENT AND TRADEMARK OFFICE
CERTIFICATE OF CORRECTION

PATENT NO. : 6,183,487 B1
DATED : February 6, 2001
INVENTOR(S) : N. Peskin et al.

It is certified that error appears in the above-identified patent and that said Letters Patent is hereby corrected as shown below:

Item [12] Inventors "Barry et al." should read -- Peskin et al. --
Item [75] Inventors "Robert Lawrence Barry, Kirkland; Matt Hefner, Puyallup; Tom Hiblar, Everett; Joseph Pearce, Seattle; Natalya Peskin, Redmond; Edward Wulfman, Woodinville, all of WA (US)" should read -- Natalya Peskin, Redmond; Edward Wulfman, Woodinville, both of WA (US) --
Item [56] Refs. Cited (Other Publs., Item 1) "Filiing Date: Aug. 19, 1999." should read -- Filing Date: Oct. 19, 1999. --
Item [56] Refs. Cited (U.S. Pats., Item 55) "5,438,630" should read -- 5,437,630 --

Signed and Sealed this

Twenty-seventh day of November, 2001

Attest:

Attesting Officer

NICHOLAS P. GODICI
Acting Director of the United States Patent and Trademark Office